US009522271B2

(12) United States Patent
Arcot-Krishnamurthy et al.

(10) Patent No.: US 9,522,271 B2
(45) Date of Patent: Dec. 20, 2016

(54) METHOD AND APPARATUS FOR CONTROLLING BLOOD PRESSURE USING RESPIRATION-MEDIATED HEART RATE VARIATION

(71) Applicant: Cardiac Pacemakers, Inc., St. Paul, MN (US)

(72) Inventors: Shantha Arcot-Krishnamurthy, Vadnais Heights, MN (US); Eric A. Mokelke, White Bear Lake, MN (US); David J. Ternes, Roseville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 143 days.

(21) Appl. No.: 14/185,751

(22) Filed: Feb. 20, 2014

(65) Prior Publication Data

US 2014/0257426 A1 Sep. 11, 2014

Related U.S. Application Data

(60) Provisional application No. 61/774,099, filed on Mar. 7, 2013.

(51) Int. Cl.
*A61N 1/00* (2006.01)
*A61N 1/36* (2006.01)
*A61B 5/024* (2006.01)
*A61B 5/08* (2006.01)

(52) U.S. Cl.
CPC ....... *A61N 1/36139* (2013.01); *A61N 1/36117* (2013.01); *A61B 5/02405* (2013.01); *A61B 5/0816* (2013.01)

(58) Field of Classification Search
CPC .... A61N 1/36117; A61N 1/36114; A61N 1/36
USPC ............................................. 607/44
See application file for complete search history.

(56) References Cited

U.S. PATENT DOCUMENTS

| | | | |
|---|---|---|---|
| 8,032,215 B2 | 10/2011 | Libus et al. | |
| 8,195,290 B2 | 6/2012 | Brockway et al. | |
| 8,244,355 B2 | 8/2012 | Bennett et al. | |
| 2008/0319513 A1* | 12/2008 | Pu | A61N 1/36114 607/62 |
| 2009/0018404 A1* | 1/2009 | Fendelander | A61B 5/0031 600/301 |

* cited by examiner

*Primary Examiner* — Amanda Patton
*Assistant Examiner* — Philip C Edwards
(74) *Attorney, Agent, or Firm* — Schwegman Lundberg & Woessner, P.A.

(57) ABSTRACT

System and methods for programming and delivering electrical stimulation to treat hypertension are described. In various embodiments, an ambulatory stimulator system, such as an implantable medical device, can detect a respiration-mediated heart rate variation (RM-HRV), monitor the efficacy of hypertension therapy and adjust the stimulation parameters using the detected RM-HRV to achieve desired therapy outcome. In some embodiments, the system can be configured to synchronize the detected heart rates to one or more respiration cycles or respiration phases within the respiration cycles, and determine the RM-HRV using the heart rates synchronized with the respiration cycles or the respiration phases. The RM-HRV may be presented to the system operator to monitor the efficacy of the AHT therapy. The ambulatory stimulator system can adjust the stimulation parameters using at least the RM-HRV.

19 Claims, 9 Drawing Sheets

METHOD AND APPARATUS FOR CONTROLLING BLOOD PRESSURE USING RESPIRATION-MEDIATED HEART RATE VARIATION

CLAIM OF PRIORITY

This application claims the benefit of priority under 35 U.S.C. §119(e) of U.S. Provisional Patent Application Ser. No. 61/774,099, filed on Mar. 7, 2013, which is herein incorporated by reference in its entirety.

TECHNICAL FIELD

This document relates generally to medical devices, and more particularly, to systems, devices and methods for closed-loop hypertension therapy using respiration-medicated heart rate variation.

BACKGROUND

Hypertension, or high blood pressure, refers to a transitory or sustained elevation of systemic arterial blood pressure to a level that is likely to induce cardiovascular damage or other adverse consequences. Hypertension has been arbitrarily defined as a systolic blood pressure above 140 mmHg or a diastolic blood pressure above 90 mmHg. For patients suffering from hypertension, the long term mortality as well as the quality of life can be improved if blood pressure can be reduced. However, many hypertension patients may not respond to treatments related to lifestyle changes or anti-hypertension drugs. Consequences of uncontrolled hypertension include, but are not limited to, retinal vascular disease and stroke, left ventricular hypertrophy, heart failure, myocardial infarction, dissecting aneurysm, and endovascular disease. Therefore, there is a need for controlling blood pressure in such patients.

SUMMARY

Electrical stimulation system can be used to treat hypertension. Examples of such electrical stimulation system can include an implantable anti-hypertension (AHT) stimulator. The AHT stimulator can be configured to stimulate a pressoreceptor region such as a baroreceptor. Baroreceptors include afferent nerves and sensory nerve endings that are sensitive to the stretching of the wall that results from increased blood pressure from within, and function as the receptor of a central reflex mechanism that tends to reduce the pressure. Activation of baroreceptors can cause baroreflex inhibition of sympathetic nerve activity and a reduction in systemic arterial pressure by decreasing peripheral vascular resistance.

The blood pressure may be monitored to assess the efficacy of the AHT therapy, and to feedback-control the stimulation delivery to achieve desired therapy outcome. Direct measurement of blood pressure may require a blood pressure sensor either non-invasively attached to the patient or invasively implanted inside the patient's body, which poses risks to patient and/or incurs additional cost. It is therefore desirable to have a surrogate for blood pressure to assess and control the stimulation during AHT therapy.

Respiratory sinus arrhythmia (RSA) is a naturally occurring variation in heart rate that occurs during a breathing cycle. During the process of RSA, inhalation temporarily suppresses vagal activity, causing an immediate increase in heart rate. Exhalation, on the contrary, increases and resumes the vagal tone. An increase in vagal tone both slows the heart and makes heart rate more variable. It is believed that RSA may be a result of baroreflex stimulation caused by changes in arterial pressure due to the regular inspiratory increase in venous return to the heart.

Various embodiments described herein improve the electrical stimulation therapy for treating chronic diseases such as hypertension. For example, a system for treating hypertension, such as an implantable AHT device, can include a stimulator configured to generate stimulation pulses. The device can include a respiration signal detector configured to sense a respiration signal. A respiration-mediated heart rate variation (RM-HRV) detector can be configured to detect variation in heart rate mediated by the respiration using the heart rates synchronized with the respiration cycles. A controller circuit can be configured to control the delivery of the stimulation pulses using the RM-HRV.

A method for treating hypertension can include sensing a physiologic signal indicative of a heart rate and detecting a plurality of heart rates from the physiologic signal, sensing a respiration signal, determining a respiration-mediated heart rate variation (RM-HRV) using the sensed respiration signal and the detected heart rates, programming one or more stimulation parameters using the RM-HRV, and delivering the programmed stimulation pulses to a target site. In some embodiments, the RM-HRV is computed from a plurality of heart rates during the inspiration phase and a plurality of heart rates during the expiration phase. The AHT therapy efficacy can be assessed by comparing a detected RM-HRV during the stimulation to a threshold indexed by the patient's respiration rate or patient status.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Disclosed herein are systems, devices and methods for stimulating various regions in the body in an effort to induce a desired response such as a manageable reduction in blood pressure, and detecting a physiologic response for use in monitoring the efficacy of stimulation and adjusting stimulation parameters to achieve desired therapy outcome. Various stimulation sites have been identified, such as nerve endings, nerve bundles, and baroreceptors. For example, some embodiments stimulate baroreceptor sites in the carotid sinus or pulmonary artery. Some embodiments involve stimulating either baroreceptor sites or nerve endings in the aorta, one or more chambers of the heart, fat pads of the heart, or an afferent nerve trunk such as the vagus, carotid and aortic nerves. Some embodiments stimulate afferent nerve trunks using a cuff electrode. Some embodiments stimulate afferent nerve trunks using an intravascular lead positioned in a blood vessel proximate to the nerve, such that the electrical stimulation passes through the vessel wall to stimulate the afferent nerve trunk. Some embodiments determine a respiration-mediated heart rate variation (RM-HRV) during stimulation, and use the RM-HRV to monitor the efficacy of stimulation and to adjusted stimulation to achieve desired therapy outcome. The disclosed system and methods as described in this document may also be used in other applications in additional to management of hypertension. For example, the RM-HRV may be used to monitor the efficacy of device therapies for congestive heart failure, sleep apnea, and arrhythmias, and to feedback-control the device therapy to achieve desired therapy outcome.

Figure 1:
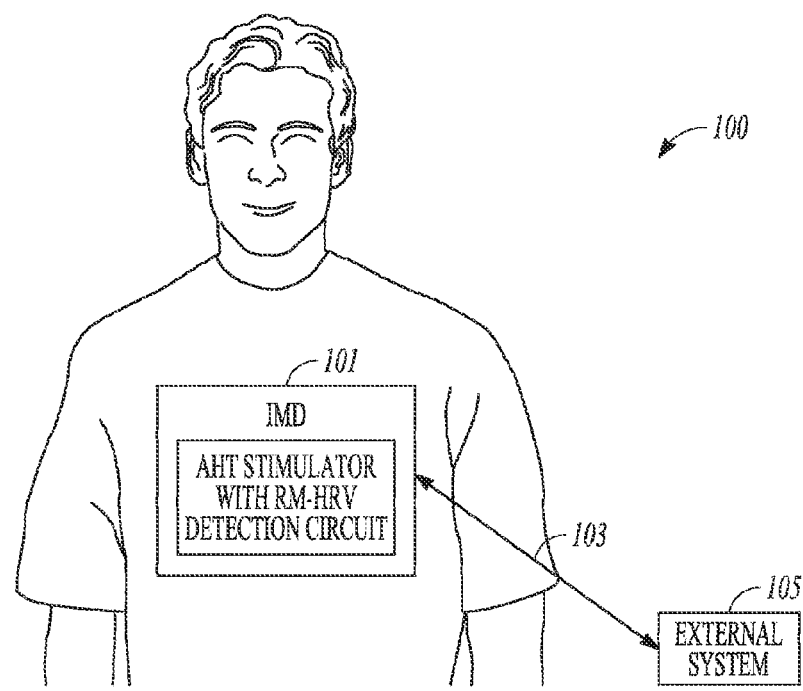
FIG. 1 illustrates, by way of example, an embodiment of an implantable stimulator system and portions of the environment in which the implantable stimulator system operates.

FIG. 1 illustrates, by way of example, an embodiment of an implantable stimulator system 100 and portions of the environment in which the implantable stimulator system 100 operates. The implantable stimulator system 100 includes an implantable medical device (IMD) 101 and an external system 105 that communicates with the IMD 101 via a communication link 103.

In some embodiments, the IMD 101 can include an implantable neural stimulator configured to generate and deliver stimulation pulses to a target site on or within the body. The implantable neural stimulator may be configured to provide anti-hypertension (AHT) therapy to treat hypertension. In various embodiments, the IMD 101 can include a neural stimulation (NS) subsystem and a cardiac rhythm management (CRM) subsystem. The NS subsystem and the CRM subsystem can include two separate devices, or two separate circuits within the IMD 101. The NS subsystem can include circuits and instructions to generate and deliver the stimulation pulses to one or more target neural stimulation sites. In some embodiments, as illustrated in FIG. 1, the NS subsystem includes an anti-hypertension (AHT) stimulator with respiration-mediated heart rate variation (RM-HRV) detection circuit. The RM-HRV detection circuit can provide a measure of RM-HRV which can be used by the AHT stimulator to feedback-control the generation and delivery of the AHT stimulation. The CRM subsystem can include circuits and instructions to generate and deliver the cardiac therapies to one or more target cardiac therapy sites. In some embodiments, the CRM subsystem can provide cardiac pacing, cardiac resynchronization, cardioversion, cardiac defibrillation, or other cardiac therapies. The IMD 101 can also include one or more monitoring or therapeutic devices, subcutaneously implanted device, a wearable external device, a drug delivery device, a biological therapy device, and other ambulatory medical devices.

Various embodiments of IMD 101 deliver therapy, such as electrical stimulation pulses, to the target sites via a therapy delivery system. The delivery system can include one or more leads coupled to the IMD 101. Each lead may include one or more electrodes along the lead body. In some embodiments, the lead may be external to the patient, and the electrodes on the leads can be placed in and affixed to a target stimulation site on the patient's skin. In some embodiments, the lead can be subcutaneously or transvenously placed inside the patient, and the electrodes can be placed to a target stimulation side internal to the patient. The leads can be temporarily placed or chronically implanted. In some embodiments, the therapy delivery system may include wireless stimulation using acoustic, radio-frequency, microwave, or other forms of energy other than electricity pulses.

The target stimulation site can be a baroreceptor region such as an aortic arch, carotid sinuses of the left and right internal carotid arteries, a carotid body, cardiac fat pads, and vena cava. Additionally, a baroreceptor region may include afferent nerve trunks, such as the vagus, aortic and carotid nerves, leading from the sensory nerve endings. Stimulating baroreceptors inhibits sympathetic nerve activity and reduces systemic arterial pressure by decreasing peripheral vascular resistance and cardiac contractility.

In various embodiments, the implantable stimulator system 100 can sense a physiological signal from the patient. The IMD 101, either alone or in combination with the external system 105, can be configured to monitor and assess the effectiveness of stimulation pulses in capturing the tissue at the target stimulation site while causing no trauma to the tissue. The physiologic signal can be obtained from an external physiologic sensor, an internal physiologic sensor, or a physiologic sensor contained within the IMD 101. The physiologic signal can be coupled to the IMD 101 or transmitted to the external system 105. In some embodiments, the electrodes used for stimulating the target site can also be configured to sense the physiologic signal. Examples of the physiological signals include electrocardiogram, electrograms, arterial pressure, pulmonary artery pressure, RV pressure, LV coronary pressure, coronary blood temperature, blood oxygen saturation, heart sounds, respiration signals, and nerve activity. The IMD 101 can include circuits to analyze the sensed physiologic signals and adjust the stimulation pulses or re-schedule the delivery the stimulation pulses through a feedback-control system.

The external system 105 can be configured to allow for programming the IMD 101 and receiving the signals acquired by the IMD 101 via a communication link 103. In an embodiment, the external system 105 can be a programmer. In another embodiment, the external system 105 can be a remote patient management system that monitors patient status or adjusts therapies from a remote location. The programmer 105 can include a user-interface configured to present to the system operator (such as a clinician) the information about patient status and system status. Alternatively or additionally, the programmer 105 can include a user-input device configured to enable the system operator to program the IMD 101 such as adjusting the parameters of the AHT therapy.

The communication link 103 can provide for data transmission between the IMD 101 and the external system 105. Examples of the communication link 103 include an inductive telemetry link, a radio-frequency telemetry link, or a telecommunication link such as an internet connection. The data transmitted through the communication link 103 can include, for example, physiological data acquired by IMD 101, therapy history data, data representing the operational status of the IMD 101, battery status, instructions to the IMD 101 such as data acquisition, sensor and sensing electrodes configuration, device self-diagnostic test, or delivery of therapy.

In various embodiments, the IMD 101 and the external system 105, including their various elements discussed in this document, are implemented using a combination of hardware and software. In various embodiments, each element of IMD 101 and external system 105 discussed in this document may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof. For example, a "comparator" can include, among other things, an electronic circuit comparator constructed to perform the only function of a comparison between two signals or a portion of a general-purpose circuit driven by a code instructing that portion of the general-purpose circuit to perform the comparison between the two signals.

Figure 2:
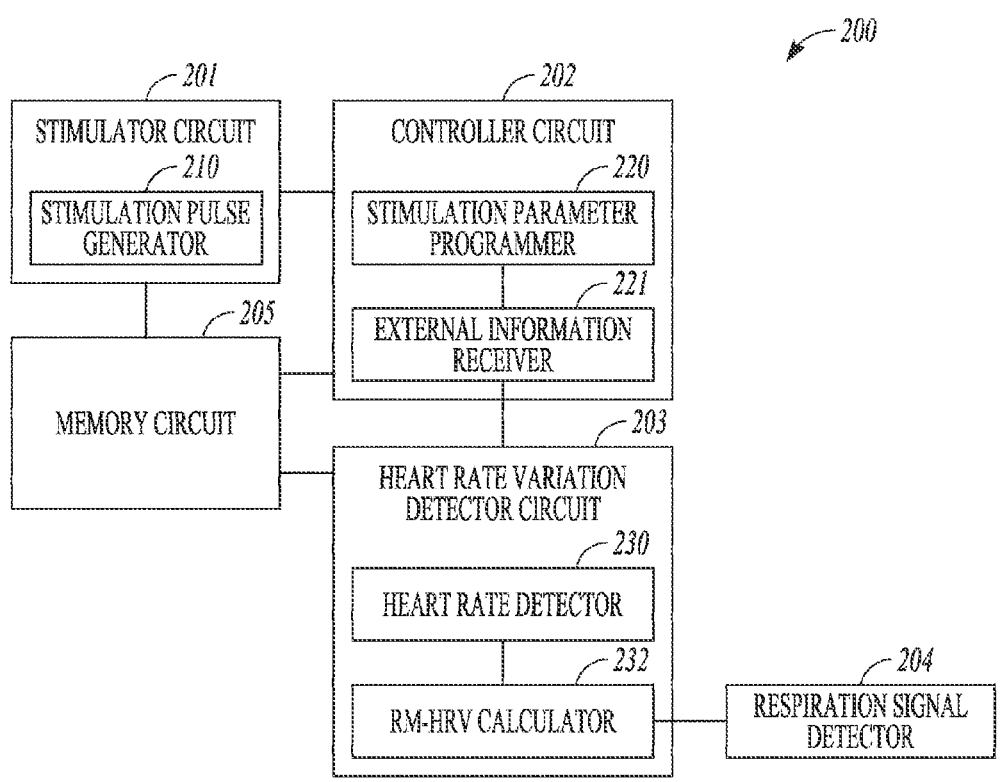
FIG. 2 illustrates, by way of example, an embodiment of an anti-hypertension (AHT) stimulator system.

FIG. 2 illustrates, by way of example, an embodiment of an AHT stimulator system 200 for treating hypertension. In various embodiments, the system 200 can be configured to be implemented in a bed-side AHT system, or in an ambulatory AHT device such as the IMD 101 or an NS subsystem of the IMD 101. The system 200 can also be configured as an acute testing and monitoring system such as in a clinical setting. Examples of the acute testing include finding desirable target stimulation site, optimizing one or more stimulation parameters for an ambulatory AHT device during device implant, and diagnosing and reprogramming the device during follow-up.

As illustrated in FIG. 2, the AHT stimulator system 200 can include a stimulator circuit 201, a controller circuit 202, a heart rate variation detector circuit 203, a respiration signal detector 204, and a memory circuit 205. The stimulator circuit 201 includes a stimulation pulse generator 210 configured to generate electrical stimulation pulses. The controller circuit 202 can be configured to be connected to the stimulator circuit 201, the heart rate variation detector circuit 203, and the memory circuit 205. In various embodiments, the controller circuit 202 can control the stimulator circuit 201 to generate stimulation pulses and schedule the delivery of the stimulation pulses.

The controller circuit 202 can include a stimulation parameter programmer 220 and an external information receiver 221. The stimulation parameter programmer 220 can be configured to adjust one or more programmable stimulation parameters stored in the memory circuit 205 when certain condition is met. Examples of the stimulation parameters include stimulation pulse strength parameters, pulse waveform or morphology, and stimulation scheduling parameters. Examples of the stimulation pulse strength parameters include a pulse amplitude, pulse width, pulse morphology, inter-pulse interval, pulse duty cycle, and pulse frequency. Pulse morphology includes one or more of a square wave, triangle wave, sinusoidal wave, and waves with desired harmonic components to mimic white noise such as indicative of naturally-occurring baroreflex stimulation. The pulses may be of one of multiphasic waves including biphasic, triphasic, or multiphasic waves. The therapy schedule parameters can control the time and duration of the stimulation pulse train. Examples of the therapy schedule parameters include a therapy-on period during which the stimulation pulses are programmed to be delivered, a therapy-off period during which no stimulation pulse is programmed to be delivered, and a therapy on-off pattern including an arrangement of therapy-on periods and the therapy-off periods.

In various embodiments, the stimulation parameter programmer 220 can be used to adjust the programmable stimulation parameters using the external information provided through the external information receiver 221. For example, the controller circuit 202 may receive from the external information receiver 221 one or more of a patient's physiologic information, system status information, and other environmental or contextual information. If at least some of the external information indicates a change of patient status or a change of system status that meets a specified criterion, the stimulation parameter programmer 220 can automatically adjust the one or more stimulation parameters. Examples of the automatic stimulation parameter adjustment using patient and system status information are discussed below, such as with reference to FIG. 6.

In some embodiments, the external information receiver 221 can include a circuit for use to communicate with a programmer or another external or internal device via a wired or wireless communication link such as an inductive or radio-frequency telemetry link. From the programmer or the external or internal device, the controller circuit 202 may receive from the external information receiver 221 a system operator's programming input. In some embodiments, the programmer or the external device can include a user-interface enabled to present to the system operator (e.g., a clinician) the information about patient status and system status. The programmer or the external device can also include a user input device enabled the system operator to program or adjust the one or more stimulation parameters.

In some embodiments, the stimulation parameter programmer 220 can chronically adjust the one or more stimulation parameters when the external information receiver 221 receives the information such as patient's newly developed or worsened disease, medical procedure performed, or environmental change. In some embodiments, the stimulation parameter programmer 220 can adjust the one or more stimulation parameters regularly or periodically. In some embodiments, the stimulation parameter programmer 220 can select from a number of values for a stimulation parameter pre-stored in the memory circuit 205.

The heart rate variation detector circuit 203, coupled to the controller circuit 202 via the external information receiver 221, can be configured to determine a heart rate variation signal and makes it available for use by the controller circuit 202. The heart rate variation detector 203 includes a heart rate detector 230 and a respiration-mediated heart rate variation calculator 232. The heart rate detector 230 can be configured to sense a physiologic signal indicative of a heart rate and detect a plurality of heart rates during the delivery of the stimulation pulses to the target site. In some embodiments, the heart rate detector 230 includes a sensor circuit coupled to one or more electrodes associated to the patient. The electrode may be placed subcutaneously or transvenously and sense a physiologic signal. The physiological signal indicative of a heart rate includes, for example, an electrocardiogram, an intracardiac electrogram, or a cardiac mechanical activation signal. The respiration-mediated heart rate variation calculator 232, coupled to the heart rate detector 230, can be configured to determine a respiration-mediated heart rate variation (RM-HRV) using at least the detected heart rates provided by the heart rate detector 230.

The heart rate variation detection circuit 203, coupled to the memory circuit 205, can transmit the RM-HRV to the memory circuit 205 for storage. The heart rate variation detection circuit 203 can pass the RM-HRV to the controller circuit 202 via the external information receiver 221. The stimulation parameter programmer 220 can be configured to adjust the stimulation parameters using the RM-HRV. For example, the stimulation parameter programmer 220 can maintain or decrease the stimulation strength parameters if the RM-HRV exceeds a first threshold, and increase the stimulation strength if the RM-HRV falls below a second threshold.

The respiration signal detector 204, connected to the RM-HRV calculator 232, can be configured to sense respiration in a patient. The respiration signal detector 204 can sense the respiration during the delivery of stimulation pulses, or sense the respiration when no stimulation pulses are delivered. The respiration signal detector 204 may include a circuit coupled to a respiration sensor or one or more electrodes associated with the patient. The respiration sensor or the one or more electrodes can be configured to sense, for example, the air flow in the respiratory system, volume change in the lungs, or a physiologic parameter modulated by respiration. The RM-HRV calculator 232 can determine the RM-HRV using the heart rate from the heart rate detector 230 and the respiration signal from the respiration signal detector 204. Examples of the respiration-mediated heart rate variation is discussed below, such as with reference to FIGS. 5 and 6.

Figure 3A:
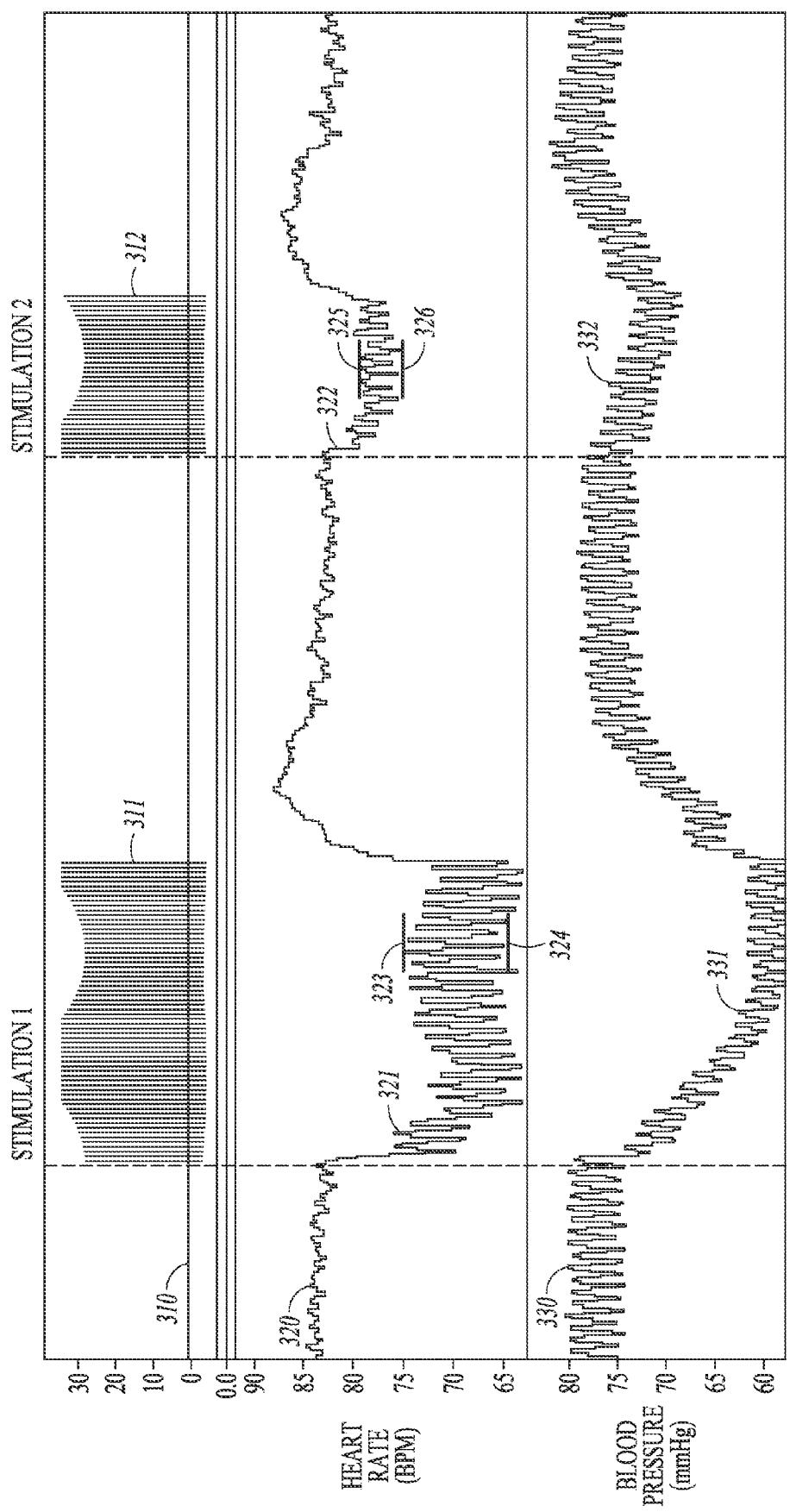
FIGS. 3A-B illustrate, by way of example, the heart rate and blood pressure responses to baroreceptor stimulation.
Figure 3B:
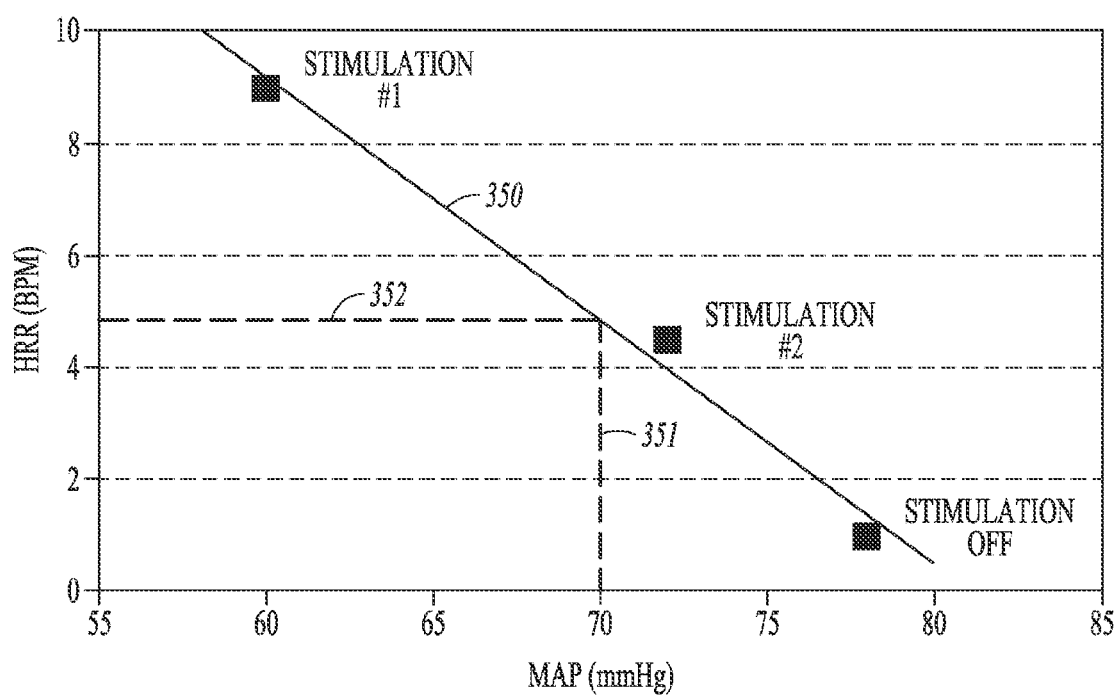

FIGS. 3A-B illustrate, by way of example, heart rate and blood pressure responses to baroreceptor stimulation. The stimulation pulses are delivered to the baroreceptor region in the exterior of the carotid artery in a canine using one or more circular electrodes placed on the region of carotid sinus. As illustrated in FIG. 3A, two stimulation pulse trains, identified as a first stimulation 311 and a second stimulation 312, were sequentially delivered to the target baroreceptor site. The first stimulation 311 is characterized by stronger stimulation intensity and lasts for a longer duration than the second stimulation 312. For example, the first stimulation 311 has an amplitude of approximately 2-6 volts, a pulse width of approximately 0.2-2.0 milliseconds, and a frequency of approximately 10-100 Hz; and the second stimulation 312 has an amplitude of approximately 0.5-5 volts, a pulse width of approximately 0.2-2.0 milliseconds, and a frequency of approximately 10-100 Hz. Before, during, and after the stimulation, heart rate signal 320 and blood pressure signal 330 were simultaneously monitored and recorded. As illustrated, prior to the stimulation, the heart rate 320 has an average of approximately 80-85 beats per minute (bpm), and short-time heart rate range (HRR), defined as the difference between the maximal heart rate and the minimal heart rate within a short period of time, is approximately 1-2 bpm. The mean blood pressure (MAP), as indicated in the blood pressure signal 330, maintains at approximately 75-80 mmHg. During the first stimulation 311, average heart rate 321 decreases to approximately 65-75 bpm after a short transient response immediately following the onset of the stimulation. At the same time, the short-time HRR (i.e., the difference between the peak heart rate 323 and the trough heart rate 324) increases to approximately 8-10 bpm. The blood pressure signal 331 during the first stimulation also decreases to approximately 60 mmHg following a transient period longer than that in heart rate 321. Following the termination of the first stimulation, the mean heart rate increases and the HRR reduces almost instantaneously. The blood pressure recovers gradually to a level comparable to the pre-stimulation level. Following the onset of the second stimulation 312, the heart rate 322 reduces to approximately 75-78 bpm in average, and the HRR increases to approximately 4-5 bpm as compared to pre-stimulation HRR of approximately 1-2 bpm. The blood pressure 332 during the second stimulation also reduces from the pre-stimulation level to 70-75 mmHg.

FIG. 3B illustrates the relationship between the heart rate variation, represented by HRR, and the mean arterial pressure (MAP) before and during the two stimulation trains as shown in FIG. 2A. A regression line 350 is generated using the data pairs (MAP, HRR) during different stimulation conditions. Other examples of regression may be created using the data pairs (MAP, HRR), such as power regression, polynomial regression, logistic regression and exponential regression. As illustrated in FIG. 3B, HRR is inversely proportional to the MAP in response to different stimulation conditions. That is, a stronger stimulation would result in low blood pressure and a large heart rate variation. The inverse relationship between MAP and the heart rate variation suggests that the heart rate variation may be used as a surrogate for blood pressure to monitor the changes in the blood pressure and to control the delivery of AHT therapy. For example, as illustrated in FIG. 3B, the AHT therapy can be deemed effective if the blood pressure falls below a MAP threshold 351 during the stimulation to the target site. According to FIG. 3B, the MAP threshold for effective therapy (for example, 70 mmHg as illustrated in FIG. 3B) corresponds to an HRR threshold 352 (which is approximately 5 bpm as illustrated in FIG. 3B). Therefore, an AHT stimulation therapy would be considered effective in reducing the blood pressure if the detected HRR during the stimulation exceeds the HRR threshold 352.

Figure 4:
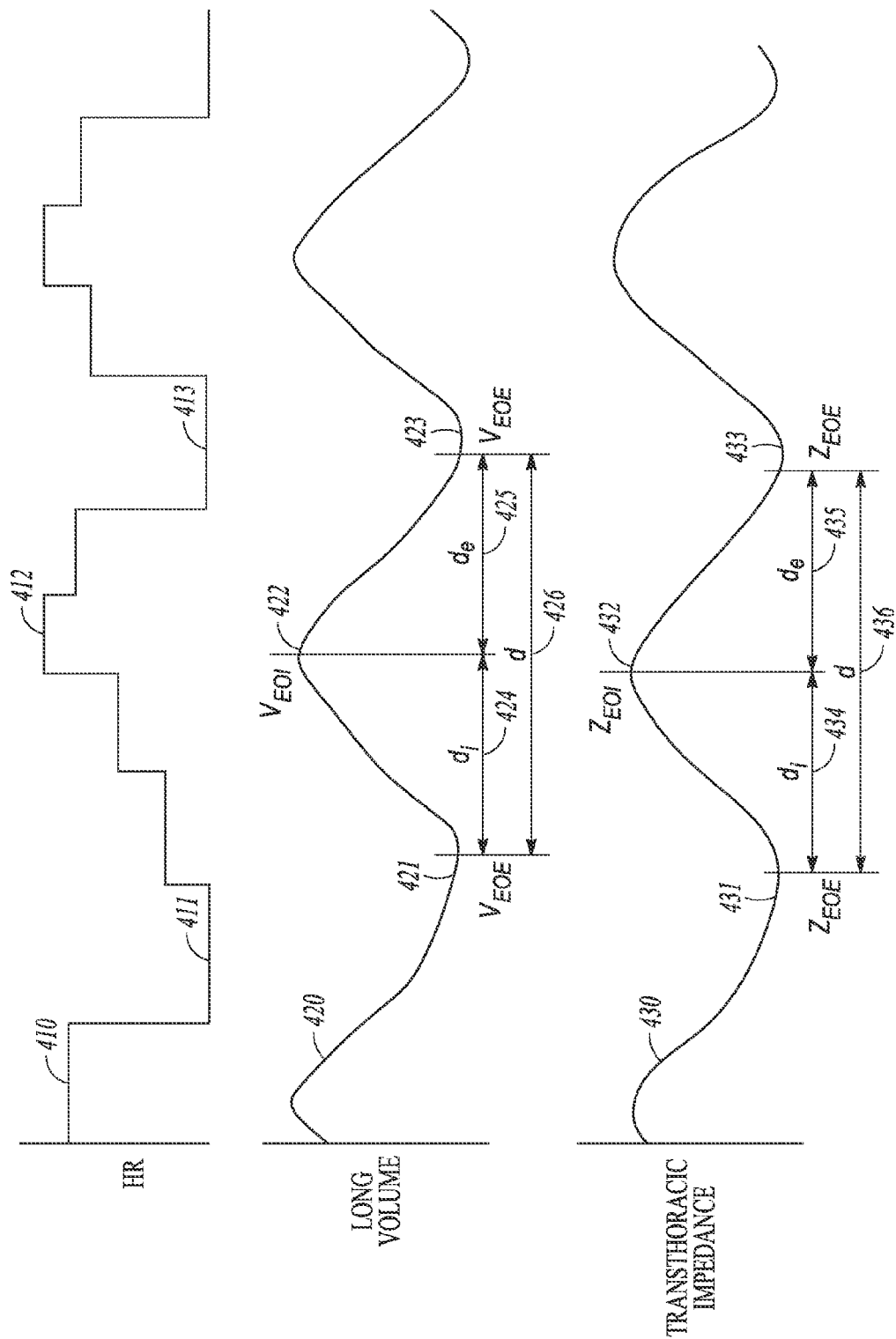
FIG. 4 illustrates, by way of example, physiologic responses to respiratory sinus arrhythmia.

FIG. 4 illustrates, by way of example, physiologic responses to a respiratory sinus arrhythmia. The heart rate signal 410 co-varies with a lung volume signal 420 and a transthoracic impedance signal 430. Both the lung volume signal 420 and the transthoracic impedance signal 430 show the cyclic variation of respiration. The transthoracic impedance may be measured using electrodes attached to or implanted in the patient. Each respiration cycle may comprise an inspiration phase and an expiration phase. At end of expiration state 421, the lung volume reaches its nadir $V_{EOE}$. Inspiration phase 424 starts from the end of expiration 421, and the lung volume gradually increases till the end of the inspiration 422 at which the lung volume reaches the peak value $V_{EOI}$. The inspiration phase 424 spans from $V_{EOE}$ at 421 to $V_{EOI}$ at 322, lasting for duration of $d_i$. Transthoracic impedance signal 430 follows a cyclic pattern similar to the changes in lung volume signal 420 during inspiration phase. At 431, corresponding to the lowest lung volume $V_{EDE}$, the transthoracic impedance reaches it minimum $Z_{EOE}$. During the inspiration phase 434, the transthoracic impedance gradually increases as the lung volume increases until the impedance reaches its maximum $Z_{EOI}$ at the end of inspiration, at which the lung volume also reaches its maximum $V_{EOI}$. Inspiration temporarily increases venous return, unloads the baroreceptors on aortic arch, carotid sinus and other baroreceptor regions, and thereby suppresses vagal activity. As a result, during the inspiration phase the heart rate increases from the lowest level 411 at the end of expiration to the peak level 412 at the end of inspiration.

Following the end of the inspiration, an expiration phase 425 commences at 422 and lasts for duration of $d_e$ till the end of the expiration phase 423. The lung volume gradually decreases from $V_{EOI}$ at the end of inspiration to $V_{EOE}$ at the end of expiration. Following a similar trend, the transthoracic impedance decreases from $Z_{EOI}$ at the end of inspiration to $Z_{EOE}$ at the end of expiration. Expiration temporarily increases the blood outflow from the heart (cardiac output) at least in part due to the diaphragm elevation and compression on the ventricles of heart. The increased cardiac output increases the pressure exerted onto the baroreceptors, and thereby increasing the vagal activity via a baroreflex control mechanism. As a consequence, during the expiration phase, the heart rate decreases from its peak 412 to the trough 413. Then, the next respiration cycle follows and the co-variation between respiration and the heart rate continues.

Respiration cycle period, denoted by d, can be computed as the duration between two time instants that represent the same state of respiration. For example, the respiration cycle period can be determined from the lung volume signal 420 as the duration between $V_{EOE}$ at 421 and $V_{EOE}$ at 423. The respiration cycle period can also be determined from the transthoracic impedance signal 430 as the duration between the end-of-expiration impedance $Z_{EOE}$ 431 and the next end-of-expiration impedance $Z_{EOE}$ 433. As illustrated in FIG. 4, the respiration cycle period d is equal to the sum of the inspiration duration $d_i$ and the expiration duration $d_e$.

Figure 5:
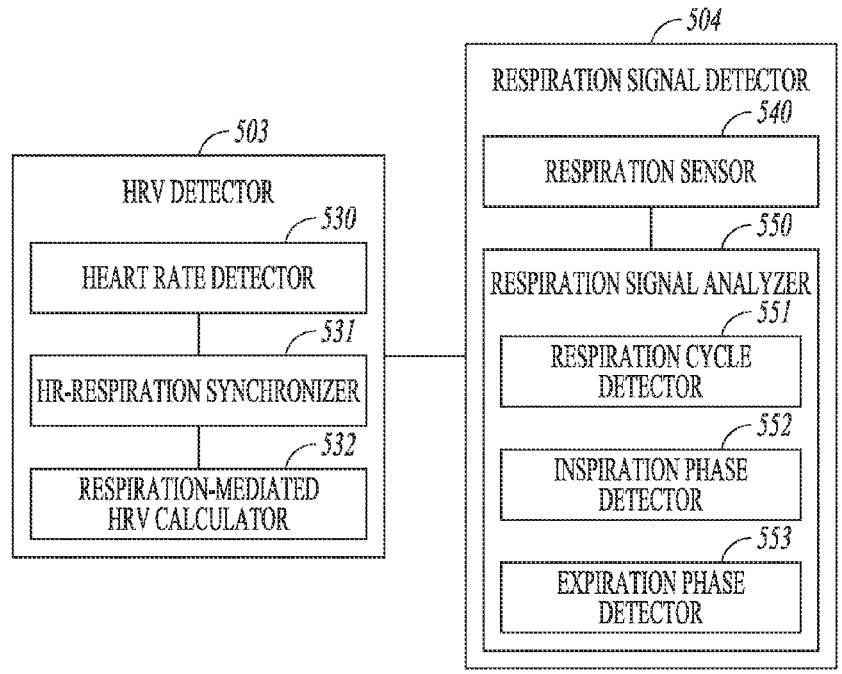
FIG. 5 illustrates, by way of example, an embodiment of heart rate variation detector and an embodiment of respiration signal detector.

FIG. 5 illustrates, by way of example, an embodiment of the heart rate variation detector 503 and an embodiment of the respiration signal detector 504. The heart rate variation detector 503 represents an embodiment of the heart rate variation detector 203, and the respiration signal detector 504 represents an embodiment of the respiration signal detector 204.

The respiration signal detector 504 includes a respiration sensor 540 and a respiration signal analyzer 550. The respiration sensor 540 may be coupled to electrodes attached to or implanted in the patient to sense the respiration signal from the patient. The respiration signal includes a respiration waveform that represents the change of air flow or lung volume during a respiration cycle. The respiration sensor 540 may be configured to sense directly the air flow in the respiratory system or volume change in the lungs, or to sense a physiologic parameter modulated by respiration, such as transthoracic impedance. In various embodiments, the transthoracic impedance can be measured using electrodes on at least one subcutaneous or transvenous lead, or electrodes attached to the skin, where the lead is coupled to an impedance sensing circuit in a bedside or ambulatory medical system, including a wearable or implantable medical device (IMD). In an embodiment, an implantable medical device (IMD) houses an impedance sensing circuit coupled to a right ventricular (RV) lead and the can housing of the IMD positioned in the left or right pectoral region, and a transthoracic impedance signal (RV-Can impedance) can be sensed by one or more electrodes on the RV lead and the IMD can housing. Transthoracic impedance may also be sensed using other lead, including LV-Can impedance measured from electrodes from the LV lead and the can housing, RA-Can impedance measured from electrodes from the RA lead and the can housing. In some embodiments, electrodes from one than one lead may be used to sense the transthoracic impedance. For example, a transthoracic impedance may be sensed by injecting current between an electrode on the RV lead and an electrode on the RA lead, while measure the resultant voltage using an electrode on the RV lead and the can housing. Other respiration sensors have also been contemplated, including patient-external respiratory bands, respiration flowmeter, implantable or patient-external breath sound detector, blood oxygen level detector, and other sensors configured to sense a respiration-modulated physiologic signal, which can be found in Lee et al., U.S. Pat. No. 7,678,061 entitled "System and method for characterizing patient respiration", filed on Apr. 15, 2004, which is incorporated herein by reference in its entirety.

The respiration signal analyzer 550, configured to analyze the respiration signal, includes a respiration cycle detector 451, an inspiration phase detector 552, and an expiration phase detector 553. The respiration cycle detector 551 can be configured to detect one or more respiration cycles from the respiration signal and determine for each respiration cycle a respiration cycle period. The respiration cycle period can be determined as the duration between two time instants that represent the same state of respiration. For example, the respiration cycle period can be computed as the duration between the end-of-expiration states 421 and 423 as illustrated in FIG. 4. The inspiration phase detector 552 detects the end-of-expiration state and the next end-of-inspiration state, and determines the inspiration phase as the period between these two states. The expiration phase detector 553 detects the end-of-inspiration state and the next end-of-expiration state, and determines the expiration phase as the period between these two states. In some embodiments, the respiration sensor directly measures the lung volume, or indirectly measures a metric indicative of the lung volume. The end-of-expiration state can be detected as the point where the lung volume (or the metric indicative of the lung volume) is minimized within a specified detection window; and the end-of-inspiration state can be detected as the point where the lung volume (or the metric indicative of the lung volume) is maximized within a specified detection window. In another embodiment, the respiration sensor senses transthoracic impedance. As illustrated in FIG. 4, the transthoracic impedance increases when the air volume in the lungs increases (e.g., during inspiration), the end-of-expiration state can be detected as the point where the transthoracic impedance is minimized within a specified detection window; and the end-of-inspiration state can be detected as the point where the transthoracic impedance is maximized within a specified detection window.

The heart rate variation detector 503 includes a heart rate detector 530, a heart rate-respiration synchronizer 531, and a respiration-mediated HRV calculator 532. The heart rate detector 530 can be configured to sense a physiologic signal indicative of the heart rate, such as an electrocardiogram, an intracardiac electrogram, and cardiac mechanical activation signal. In some embodiments, the heart rate detector 530 and the respiration sensor 540 can receive from a physiologic sensor a physiological signal that contains both the heart rate and respiration information. For example, an electrocardiograph (ECG) can be used to determine the heart rate and the respiration. During inspiration, the diaphragm shift downwards away from the apex of the heart. The increased filling of the lungs further stretch the apex of the heart towards the abdomen. During expiration, the lung volume reduces, and the diaphragm elevates upwards toward the heart which compresses the apex of the heart towards the breast. As a result, the angle of the electric cardiac vector that gives rise to the ECG signal changes during inspiration and respiration phases, which leads to cyclic variation in R-wave amplitude on the ECG signal. The respiration signal can then be obtained from the R-wave amplitude signal using demodulation method.

The HR-respiration synchronizer 531, coupled to the heart rate detector 530 and the respiration signal detector 504, can be configured to synchronize the detected heart rates to the respiration cycles, inspiration phase, or expiration phase. The synchronization process can compensate both system lag and physiologic lag between the respiration signal and the heart rate signal. The system lag includes the lag between the heart rate detector 530 and the respiration signal detector 504 in sensing and processing the respective signals and providing the results to the HR-respiration synchronizer. In some embodiments, the HR-respiration synchronizer 531 can issue a system synchronization signal such as a pulse, and determine the system lag the lag as the pulse's signature on the heart rate signal and the pulse's signature on the respiration signal.

As illustrated in FIG. 3, the heart rate signal and the respiration signal generally co-vary with a physiologic phase lag. The physiologic phase lag may be due to the lag from the change in respiration phases to the change in HR. For example, because RSA is at least in part caused by the baroreflex system, the HR change lags behind the change in respiration phase. For example, during inspiration, thoracic pressure drops and the venous return increases, and the arterial baroreceptors are unloaded. Through the baroreflex mechanism, the vagus nerve activity is suppressed which in turn cause an increase in sinus node firing and increase in heart rate. The HR-respiration synchronizer 531 may compensate this physiologic lag such that little phase difference exists between the heart rate signal and the respiration signal.

The respiration-mediated heart rate variation (RM-HRV) calculator 532 can determine the respiration-mediated heart rate variation using the heart rates synchronized with the respiration cycles. In an embodiment, the RM-HRV includes a variance or a spreadness measure of the heart rates (or cardiac cycles such as R-R intervals) within one or more respiration cycles. In some embodiments, the respiration-mediated heart rate variation can be calculated as the heart rate variation between the heart rates during the inspiration phase and the heart rates during the expiration phase of the respiration cycle. The heart rate variation can be represented by a heart rate range (HRR) within the respiration cycles, where the HRR includes a difference between the heart rates during the inspiration phase and the heart rates during the expiration phase.

Figure 6:
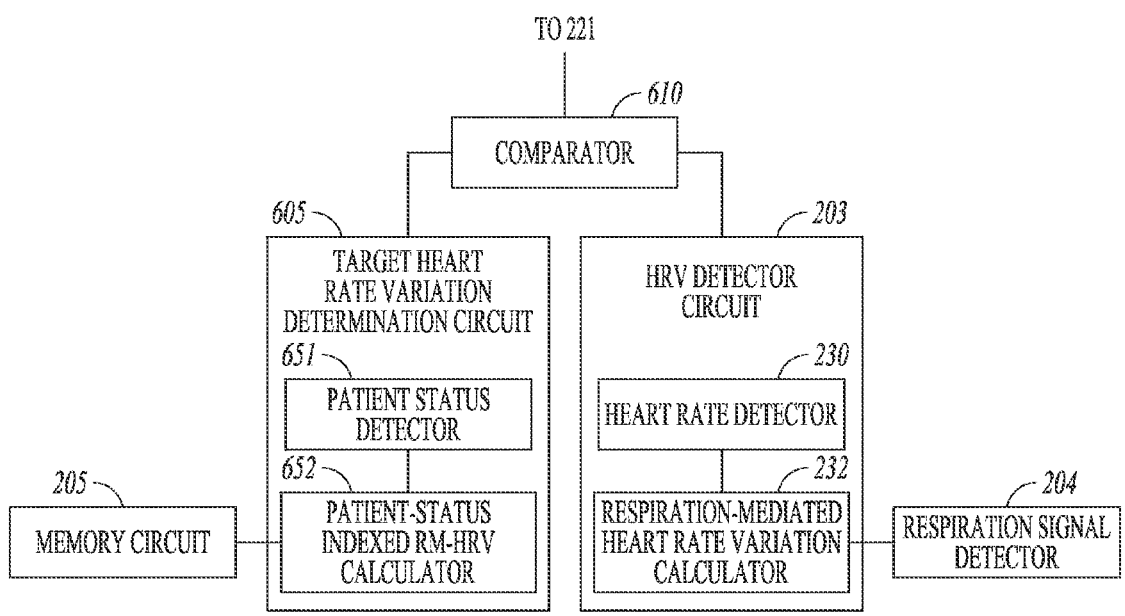
FIG. 6 illustrates, by way of example, an embodiment of feedback circuit for adjusting the stimulation parameters.

FIG. 6 illustrates, by way of example, an embodiment of the feedback circuit provided to the control circuit 202 for adjusting the one or more stimulation parameters. The external information receiver 221 can be configured to receive input from the heart rate variation detector circuit 203 and a target heart rate variation determination circuit 605. The HRV detector circuit 203 includes a heart rate detector 230 and a RM-HRV calculator 232 configured to calculate a RM-HRV using the detected heart rate from the heart rate detector 230 and the sensed respiration signal from the respiration signal detector 204.

The target heart rate variation determination circuit 605 is configured to provide a desired level of heart rate variation based on present patient status. The target heart rate variation determination circuit 605 can include a patient status detector 651 and a patient-status indexed RM-HRV calculator 652. The patient status detector 651 is configured to detect a present patient status such as a respiration rate, an activity levels, a sleeping state, a posture, or a disease state. The patient status may affect the respiration-mediated heart rate variation.

The memory 205 can be configured to store a plurality of RM-HRV levels, a set of patient status, and an association map associating each of the patient status to one of the RM-HRV level. The association map may be a look-up table, a hash table, an association map, or other data structure with searchable entries. The association map can be constructed using empirical knowledge about the impact of the patient status on the HRV value. In an embodiment, the association map includes an association between respiration rates to RM-HRV levels. Because at higher respiration rate the heart rate variability may decrease, the association map can be constructed such that a higher respiration rate is mapped to a smaller target RM-HRV level. In another embodiment, the association map includes an association between activity levels to RM-HRV levels. Because intensive activity tends to increase the sympathetic tone and decreased the parasympathetic tone, thereby reducing the heart rate variability, the association map can be constructed such that a higher activity level is mapped to a smaller target RM-HRV level.

The patient-status indexed RM-HRV calculator 652, coupled to the memory circuit 205, can determine a patient-status indexed RM-HRV level using the detected patient status and the association map. A comparator 610 can be used to compare the detected HRV provided by HRV detector circuit 203 and the target RM-HRV level provided by the target RM-HRV determination circuit 605. In an embodiment, the comparator 610 can be configured to compute a difference between the detected HRV and the target RM-HRV, and the controller circuit uses the difference to adjusting the stimulation parameters. For example, if the difference between the detected HRV and the target RM-HRV is positive and greater than a tolerance level, the detected HRV is deemed sufficiently large, and the controller circuit 202 may maintain or decrease the stimulation parameter value to reduce the stimulation strength. On the other hand, if the difference between the detected HRV and the target RM-HRV is negative and smaller than a tolerance level, the detected HRV is deemed small, and the stimulation strength is insufficient to cause desirable blood pressure reduction. The controller circuit 202 may then increase the stimulation parameter value to increase the stimulation strength. The controller may repeat the adjustment in response to the comparison between the detected HRV and the target RM-HRV until the detected respiration-mediated heart rate variation reaches the target heart rate variation.

Figures 7, 8:
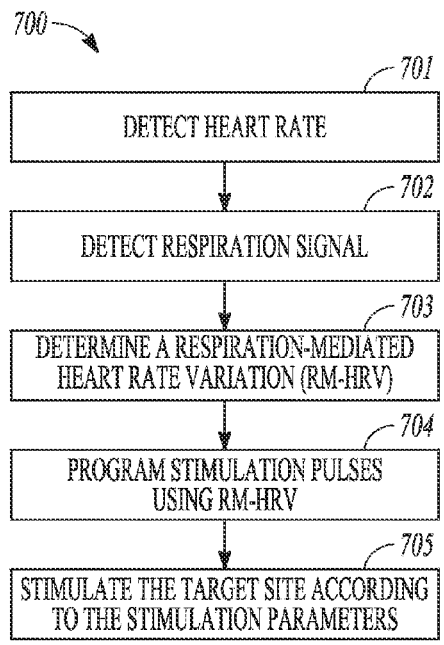
FIG. 7 illustrates, by way of example, a method for stimulating a target site to treat hypertension.
FIG. 8 illustrates, by way of example, a method for determining a respiration-mediated heart rate variation (RM-HRV).

FIG. 7 illustrates, by way of example, a method 700 for stimulating a target site to treat hypertension. In an embodiment, the implantable stimulator system 100, including its various embodiments discussed in this document, is programmed to perform the method 700, including its various embodiments discussed in this document. The method begins with detecting heart rate in a patient at 701. Detection of heart rate can include sensing a physiologic signal indicative of a heart rate and detecting from the physiologic signal a plurality of heart rates during the delivery of the stimulation pulses to the target site. In some embodiments, the physiological signal can be an electrical signal such as an electrocardiogram (ECG) or an intracardiac electrogram. In some embodiments, the physiological signal can be a cardiac mechanical activation signal such as a stress signal, a pressure signal, a heart sound signal, a cervical impedance signal, and mechanical deflection signal sensed from a carotid or other blood vessels. The physiologic signals can be acquired using one or more leads each including one or more electrodes along the lead body. The electrodes and the leads may be placed inside the body subcutaneously or transvenously, or attached to the patient non-invasively. From the physiologic signal characteristic components from the electrical signal, such as R waves or P waves in ECG or electrogram, or peak contraction or end of systole from the cardiac mechanical signal, are detected; and the heart rates can be determined from the detected characteristic components including, for example, R-R interval, P-P interval, intervals between adjacent end of systoles or between adjacent end of diastoles.

At 702, a respiration signal is detected from the patient. The respiration signal may include a respiration waveform that represents the changes of air flow or lung volume during respiration cycles. In some embodiments, the respiration signal can include a physiologic signal directly measuring air flow in the respiratory system or volume change in the lungs. In some embodiments, the respiration signal can include a physiologic parameter modulated by respiration, such as transthoracic impedance sensed by two or more electrodes placed on or within the chest, where a current can be injected into thorax using a first pair of electrodes and the resulting voltage is sensed by a second pair of electrodes. The second pair of electrodes may be different from the first pair, or the two pairs of electrodes may share one or both electrodes. In some embodiments, the electrodes used for transthoracic impedance sensing are coupled to a bedside or ambulatory medical system or device, and the electrodes may include the can housing of the ambulatory device. In some other embodiments, the respiration signal can be obtained from the ECG signal. Because the R wave amplitude may be modulated by respiration, cyclic variation in R-wave amplitude can be extracted and used as surrogate of the respiration. Other methods of acquiring a respiration signal are also contemplated, including for example, the use of patient-external respiratory bands, respiration flowmeter measurements, implantable or patient-external breath sound detection, blood oxygen levels, and other methods or processes for sensing a respiration-modulated physiologic signal. One such example is discussed in U.S. Pat. No. 7,678,061 entitled "System and method for characterizing patient respiration", assigned to Cardiac Pacemakers, Inc., which is incorporated herein by reference in its entirety.

At 703, a RM-HRV can be determined using, for example, both the detected heart rate and the detected respiration signal. The respiration signal may be analyzed to generate one or more characteristic metrics including respiration cycle period, end of inspiration, end of respiration, and inspiration phase and expiration phase within a respiration cycle. The detected heart rates may then be synchronized with the respiration signals before calculating the RM-HRV. The synchronization takes into account both the system lag and the physiologic lag between the respiration signal and the heart rate signal. Examples of the synchronization are discussed below, such as with reference to FIG. 8.

The RM-HRV at 703 can be computed using a selected number of heart rates or R-R intervals in synchrony with a respiration signal. For example, in an embodiment, timing information of the respiration phases may be used to select a plurality of heart rates within a specified respiration phase, and the RM-HRV can be computed from these heart rates. In another embodiment, the RM-HRV can be computed from a subset of the detected heart rates during which the respiration metrics meet a specified criterion. For example, the RM-HRV can be computed from the heart rates falling within the synchronized respiration cycles with a predetermined duration. The RM-HRV for the selected heart rates or R-R intervals may be computed using a method including, for example, a range, a variance, and other second or higher order statistical measurement of spreadness.

The RM-HRV can be used at 704 to program the stimulation pulses to be used in AHT therapy. In an embodiment, the programming of the stimulation pulses can be achieved by adjusting the stimulation strength parameters which control the amount of energy delivered to the target site within a unit time. The stimulation strength parameters may include pulse amplitude, pulse width, pulse waveform or morphology, inter-pulse interval, pulse duty cycle, and pulse frequency. The programmable stimulation parameters may also include therapy schedule parameters that control the time and duration of the stimulation pulse train including a therapy-on period during which the stimulation pulses are delivered, a therapy-off period during which no stimulation pulses are delivered, and a therapy on-off pattern that determines the arrangement or combination of therapy-on periods and therapy-off periods. In some embodiments, the stimulated strength parameters are maintained at their existing values or decreased if the respiration-mediated heart rate variation exceeds a first pre-determined threshold value; and the stimulated strength parameters are adjusted to increase the stimulation strength if the respiration-mediated heart rate variation is less than a second pre-determined threshold value.

The programming of the stimulation pulses at 704 can be performed automatically or by receiving programming parameters from a system operator (e.g., a clinician). In some embodiments, the stimulation parameters can be adjusted in proportion to the deviation from a pre-determined threshold. For example, if the detected RM-HRV at 703 falls below a RM-HRV threshold corresponding to a desirable blood pressure reduction, then the stimulation parameters can be adjusted such as by increasing the values of pulse frequency, pulse width, or the therapy-on time. The detected RM-HRV can be presented to the system operator via a user-interface, where the system operator can provide input command for programming the one or more stimulation parameters or to accept an automatically generated recommendation for stimulation parameter adjustment.

The adjusted stimulation pulses can then be delivered to the target site at 705. In various embodiments, the target site of stimulation include one or more of baroreceptors regions such as carotid artery, aortic arch, pulmonary arteries, coronary arteries and other anatomical locations with or close to baroreceptors. The target site of stimulation may also include vagus nerves, nerve bundles, never trunk, and other neural targets known to cause at least parasympathetic activation. The stimulation pulses may be delivered to one or more stimulation electrodes deployed at or near the target stimulation site through a stimulation channel. In some embodiments, the stimulation channel includes a lead external to the patient, or subcutaneously or transvenously implanted inside the patient's body. In other embodiments, the stimulation channel can be a wireless stimulation channel where the stimulation pulses are delivered via acoustic or radiofrequency links. In an embodiment, the stimulation electrodes are cuff electrodes wrapping around a portion of an exterior of a carotid artery where carotid baroreceptors are located. The stimulation electrodes are electrically connected to an implantable medical device via a subcutaneously implanted lead. The implant medical device can be configured to deliver the stimulation pulses to the electrodes and thereby stimulates the baroreceptors according to the responses of RM-HRV.

FIG. 8 illustrates, by way of example, a method 800 for determining a respiration-mediated heart rate variation (RM-HRV). The method 800 represents an embodiment of the method 703 of determining RM-HRV for use in AHT stimulation therapy as illustrated in FIG. 7.

The method begins at 801 with detecting heart rate from a physiologic signal indicative of electrical or mechanical activities of the heart. At 802, a respiration signal is sensed from the patient. The respiration signal may include signals indicative of air flow in the respiratory system or volume change in the lungs, or a physiologic parameter modulated by respiration such as a transthoracic impedance signal.

The sensed respiration signal is analyzed at 803 to identify respiration cycles, inspiration phases, and the expiration phases from the sensed respiration signal. In an embodiment, the respiration signal can be a transthoracic impedance signal. As illustrated in FIG. 4, the end-of-expiration state ($Z_{EOE}$) may be detected as the point where the transthoracic impedance is minimized within a specified detection window; while the end-of-inspiration state may be detected as the point where the transthoracic impedance is maximized within a specified detection window ($Z_{EOI}$). The respiration cycle period can then be determined as the duration between two time instants that represent the same state of respiration, such as the end-of-expiration states $Z_{EOE}$ at 431 and $Z_{EOE}$ at 433. An inspiration phase may also be detected as a period between the end-of-expiration state and the next end-of-inspiration state, such as the duration from $Z_{EOE}$ at 431 to $Z_{EOI}$ at 432; while an expiration phase may be detected as the end-of-inspiration state and the next end-of-expiration state, such as the duration from $Z_{EOI}$ at 432 to $Z_{EOE}$ at 435.

At 804, the detected heart rates are synchronized with the sensed respiration signal to compensate the system lag and the physiologic lag between the signals. The synchronization takes into account both the system lag and the physiologic lag between the respiration signal and the heart rate signal. The system lag may represent the lag between the heart rate detector and the respiration signal detector in sensing and processing the respective signals. The system lag may be determined by issuing a system synchronization signal (such as a pulse) and measuring the time lag between the pulse's signature on the heart rate signal and the pulse's signature on the respiration signal. The physiologic lag may represent a delay between the change in respiration and the change of HR. For example, in some cases the HR change can lag behind the change in respiration phase as a result of the delay from the respiration to the HR response through the baroreflex mechanism. The synchronization between the respiration and the heart rate signal may be performed to compensate the determined system lag and the physiologic lag between the detected heart rate signal and the detected respiration signal.

Then, at 805 a representative heart rate during inspiration is determined. In an embodiment, the heart rates or R-R intervals in synchrony with a respiration signal are grouped to a set during the detected inspiration phases of one or more respiration cycles, that is, $\{HR\_INSP(i)\}$ for $i=1, 2, \ldots, N$, where N denotes the total number of heart rates or R-R intervals in the set. The representative heart rate ($HR_i$) may be computed as the average heart rate across $\{HR\_INSP(i)\}$. Other measures of central tendency, including the median, mode, trimmed mean may also be used to determine $HR_i$. In some embodiments, the heart rate set $\{HR\_INSP(i)\}$ includes only the heart rates or R-R intervals within a specified time window around the end-of-inspiration states.

At 806 a representative heart rate during expiration is determined. In an embodiment, the heart rates or R-R intervals in synchrony with a respiration signal are grouped to a set during the detected expiration phases of one or more respiration cycles, that is, $\{HR\_EXP(j)\}$ for $j=1, 2, \ldots, M$, where M denotes the total number of heart rates or R-R intervals in the set. The representative heart rate ($HR_e$) may be computed as the average heart rate across $\{HR\_EXP(j)\}$. Other measures of central tendency, including the median, mode, trimmed mean may also be used to determine $HR_e$. In some other embodiment, the heart rate set $\{HR\_EXP(j)\}$ includes only the heart rates or R-R intervals within a specified time window around the end-of-expiration states.

Rather than using all the heart rates or R-R intervals during the inspiration or the expiration phases, in various embodiments, a selective number of heart rates or R-R intervals during the inspiration or the expiration may be selected. For example, the RM-HRV can be computed from the detected heart rates during which the synchronized respiration metrics meet a specified criterion. In an embodiment, HRV can be computed from the heart rates falling within certain synchronized respiration cycles with a predetermined respiration rate.

At 807, the RM-HRV for the selected heart rates or R-R intervals may be computed using the representative heart rates during inspiration ($HR_i$) and the representative heart rates during expiration ($HR_e$). In an embodiment, the RM-HRV can be the difference between $HR_i$ and $HR_e$. In some embodiments, the RM-HRV can be computed as a statistical distance between the heart rate sets $\{HR\_INSP(i)\}$ and $\{HR\_INSP(i)\}$ using $HR_i$, $HR_e$ and the covariance matrix of at least one of $\{HR\_INSP(i)\}$ or $\{HR\_INSP(i)\}$.

Figure 9:
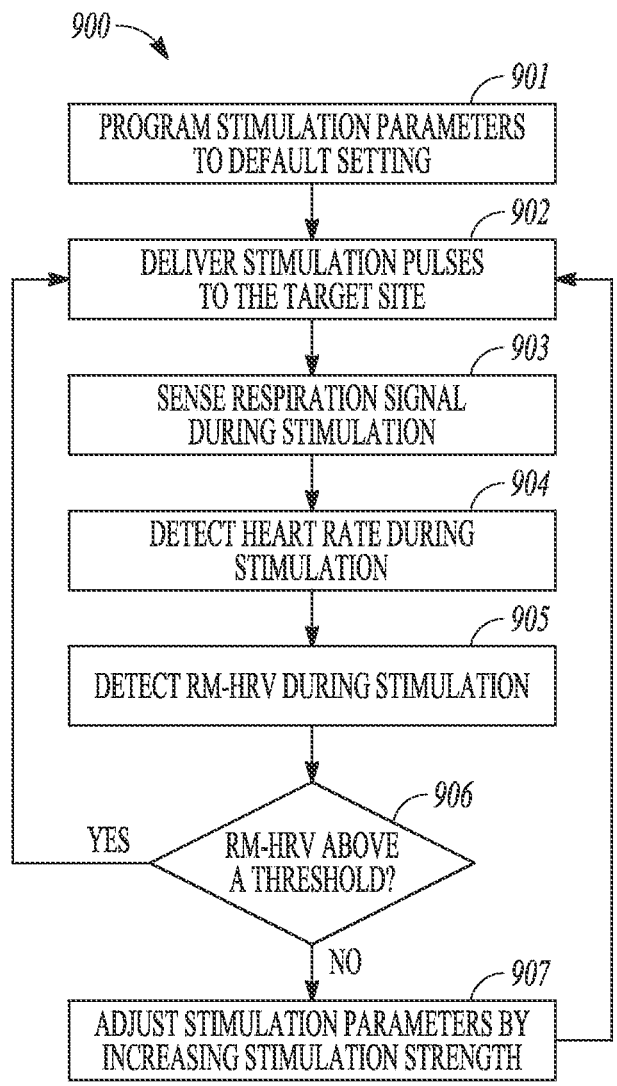
FIG. 9 illustrates, by way of example, a method for stimulating a target site to treat hypertension.

FIG. 9 illustrates, by way of example, a method 900 for stimulating a target site to treat hypertension. The method 900 represents an embodiment of the method 700 for AHT stimulation therapy. The method begins with programming one or more stimulation parameters to a default setting at 901. The default setting may include empirical parameter values that are expected to be effective in causing a therapeutic effect or clinically meaningful reduction in blood pressure. The default values may be determined according to patient's health status and disease records, the patient's AHT therapy history, or population-based record of AHT treatment. In some embodiments, the default stimulation comprises of a train of pulses with variable stimulation strength. For example, the pulse frequency or pulse amplitude gradually increases from a smaller first value to a larger second value.

At 902, stimulation pulse train is delivered to the target site according to the default programming parameters. During the delivery of the stimulation pulses, a respiration signal is sensed at 903 and heart rates are detected at 904. In some embodiment, the respiration signal can be acquired using a flowmeter that senses the air flow in the respiratory system or air volume change in the lungs during respiration. In other embodiments, the respiration signal can be acquired using a physiologic sensor that senses a physiologic parameter modulated by respiration, such as a transthoracic impedance signal sensed by two or more electrodes attached to or implanted inside a patient's body. The heart rate during stimulation can be detected at 904 using heart rate sensors such as electrocardiograph (ECG), intracardiac electrogram, and cardiac mechanical activation signals. The respiration signal and the heart rate can be determined from a common physiologic signal that contains both the heart rate and the respiration information, such as an ECG signal.

At 905, a respiration mediated heart rate variation (RM-HRV) is detected. The detection of RM-HRV may include synchronizing the detected heart rates with the sensed respiration signal and calculating a variation metric using the heart rates synchronized with the respiration signal. In some embodiments, The RM-HRV may be determined using the method 800. The detected RM-HRV is then compared to a threshold or a desirable HRV range at 906. The threshold or the desirable range indicates the desired amount of reduction in blood pressure, and thereby the effectiveness of the AHT therapy. In an example as illustrated in FIG. 3B, the threshold of the RM-HRV, represented by HRR threshold 352, corresponds to a mean blood pressure threshold 351 of 70 mmHg. The stimulation therapy is deemed effective when then BP drops below 70 mmHg.

If the RM-HRV level is above the threshold level or within the desirable range, then the present stimulation is deemed effective, and the stimulation can be continued without parameter adjustment. Alternatively, the stimulation strength can be reduced to conserve the power consumption without compromising the therapy efficacy. If the RM-HRV level is below the threshold level or outside the desirable range, then the present stimulation is deemed ineffective; and the stimulation parameters can be adjusted at 907 by increasing the stimulation strength. The stimulation strength may be increased by increasing the pulse frequency, pulse width, or the therapy-on time. The stimulation parameters can be automatically adjusted. In some embodiments, the detected RM-HRV may be presented to the system operator via a user-interface, and the system operator may manually program the one or more stimulation parameters or accept an automatically generated recommendation for stimulation parameter adjustment through a user input device. Stimulation pulses may then be delivered at 902 according to the adjusted stimulation parameters.

Figure 10:
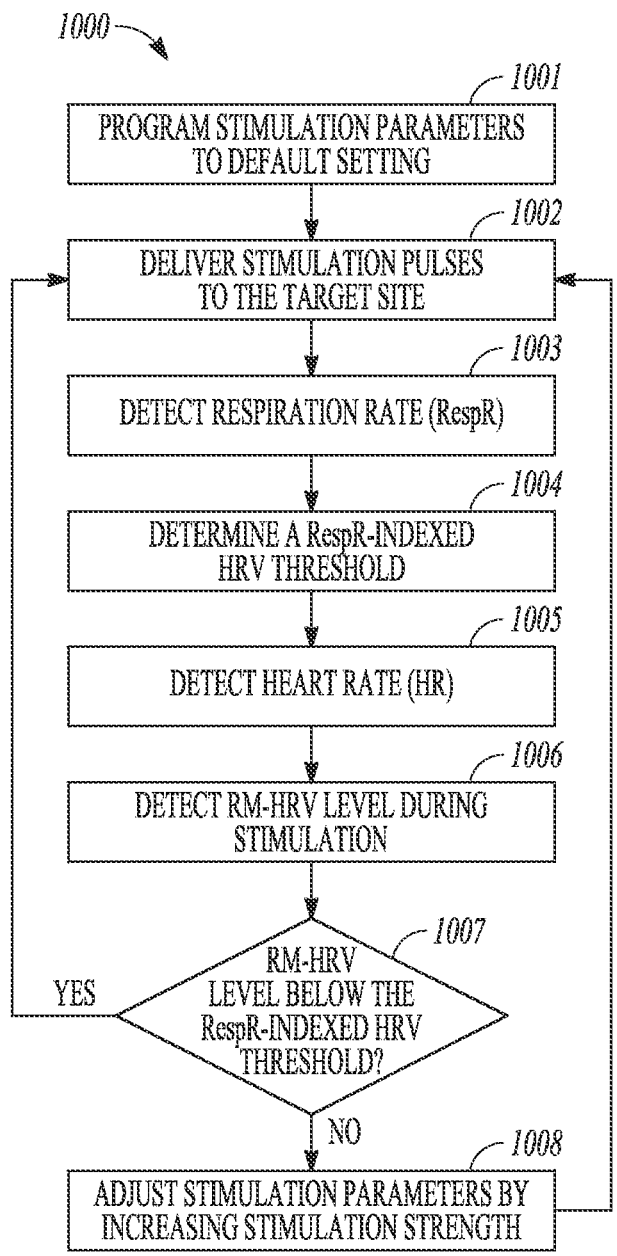
FIG. 10 illustrates, by way of example, a method for stimulating a target site to treat hypertension using patient respiration rate-indexed RM-HRV.

FIG. 10 illustrates, by way of example, a method 1000 for stimulating a target site to treat hypertension using patient respiration rate-indexed RM-HRV. The method 1000 represents an embodiment of the method 700 for AHT stimulation therapy. The method starts with programming one or more stimulation parameters to a default setting at 1001. The default setting may include empirical stimulation parameter values that are expected cause a therapeutic effect or clinically meaningful reduction in blood pressure. The default values can be determined using the patient's health status, disease records, the AHT therapy history, or population-based AHT therapy.

At 1002, stimulation pulses are delivered to the target site according to the programmed stimulation parameters. During the stimulation, at 1003, a respiration signal is sensed and a respiration rate can be determined during the stimulation. The acquired respiration signal may include cyclic variation of signal morphology, from which various respiration metrics may be determined. In an embodiment, the respiration signal can include a transthoracic impedance signal. From the transthoracic impedance signal, end-of-inspiration states (such as $Z_{EOI}$ 432 in FIG. 4) may be detected as the peaks of the transthoracic impedance signal; and end-of-expiration states may be detected as the troughs of the transthoracic impedance signal (such as $Z_{EOE}$ 431 and $Z_{EOE}$ 433 in FIG. 4). The respiration rate (RespR) can be determined at 1003 as the reciprocal of the respiration cycle period determined, for example, as the duration between two adjacent end-of-expiration states. At 1004, a respiration-rate indexed HRV threshold ($HRV_T$) can be determined such as using the detected respiration rate. $HRV_T$ indicates the desired amount of reduction in blood pressure for an effective AHT therapy under a particular respiration rate. In various embodiments, $HRV_T$ can be chosen to be inversely proportional to the respiration rate, that is, a lower $HRV_T$ can be chosen for a high respiration rate; and a higher $HRV_T$ can be chosen for a low respiration rate. In some examples, $HRV_T$ can be determined by refereeing to a RespR-$HRV_T$ map stored such as in the memory circuit 205. The RespR-$HRV_T$ map may comprise a plurality of values or value ranges of respiration rate, each being mapped to a threshold value $HRV_T$. In some embodiments, the RespR-$HRV_T$ map can be constructed such that a higher respiration rate maps to a smaller $HRV_T$ value. The RespR-$HRV_T$ map can be implemented as a look-up table, a hash table, an association map, or other data structures.

During the stimulation, the heart rate is sensed at 1005 from a heart rate sensor. At 1006, the detected heart rates and the metrics from the sensed respiration signal, including the inspiration phase and expiration phase of respiration cycles, are used to detect the RM-HRV level during the stimulation. In an embodiment, the RM-HRV can be determined using the method 800. In some embodiments, in determining the RM-HRV level, the respiration signal and the heart rates are synchronized; and only the detected heart rates or intervals during the respiration cycles with specified duration are used in computing the RM-HRV. In one example, assuming the detected respiration rate at 1003 is $R_0$ Hz (or equivalently 60*$R_0$ breaths per minute), which corresponds to a respiration cycle of $d_0=1/R_0$ seconds. Then during a sequence of N respiration cycles with cycle period d(i) (where i=1, 2, . . . , N), only those heart rates or R-R intervals that occur during the respiration cycles of duration greater than $d_0-\Delta$ but shorter than $d_0+\Delta$ are selected to determine the RM-HRV during stimulation, where $\Delta$ is a tolerance of the respiration duration. This method of selecting heart rates ensures that the computed RM-HRV is minimally affected by large variations of the respiration rate.

The detected RM-HRV during stimulation is then compared to the respiration rate indexed HRV threshold ($HRV_T$) at 1007. If the RM-HRV level is above the respiration rate indexed threshold $HRV_T$, then the present stimulation is deemed effective, and the stimulation can be continued at 1002 without parameter adjustment. Alternatively, the stimulation strength may be reduced to conserve the power consumption without compromising the therapy efficacy. The stimulation therapy is then resumed at 1002 according to the adjusted stimulation parameters. If the RM-HRV level is below the respiration rate indexed threshold $HRV_T$, then the therapy is deemed ineffective and the one or more stimulation parameters may be adjusted at 1008 by increasing the stimulation strength, such as by increasing the values of pulse frequency, pulse width, or the therapy-on time. The stimulation parameters can be automatically adjusted. In some embodiments, the detected RM-HRV may be presented to the system operator via a user-interface, and the system operator can manually program one or more stimulation parameters or accept an automatically generated recommendation for stimulation parameter adjustment. Stimulation can be resumed at 1002 according to the adjusted stimulation parameters.

Figure 11:
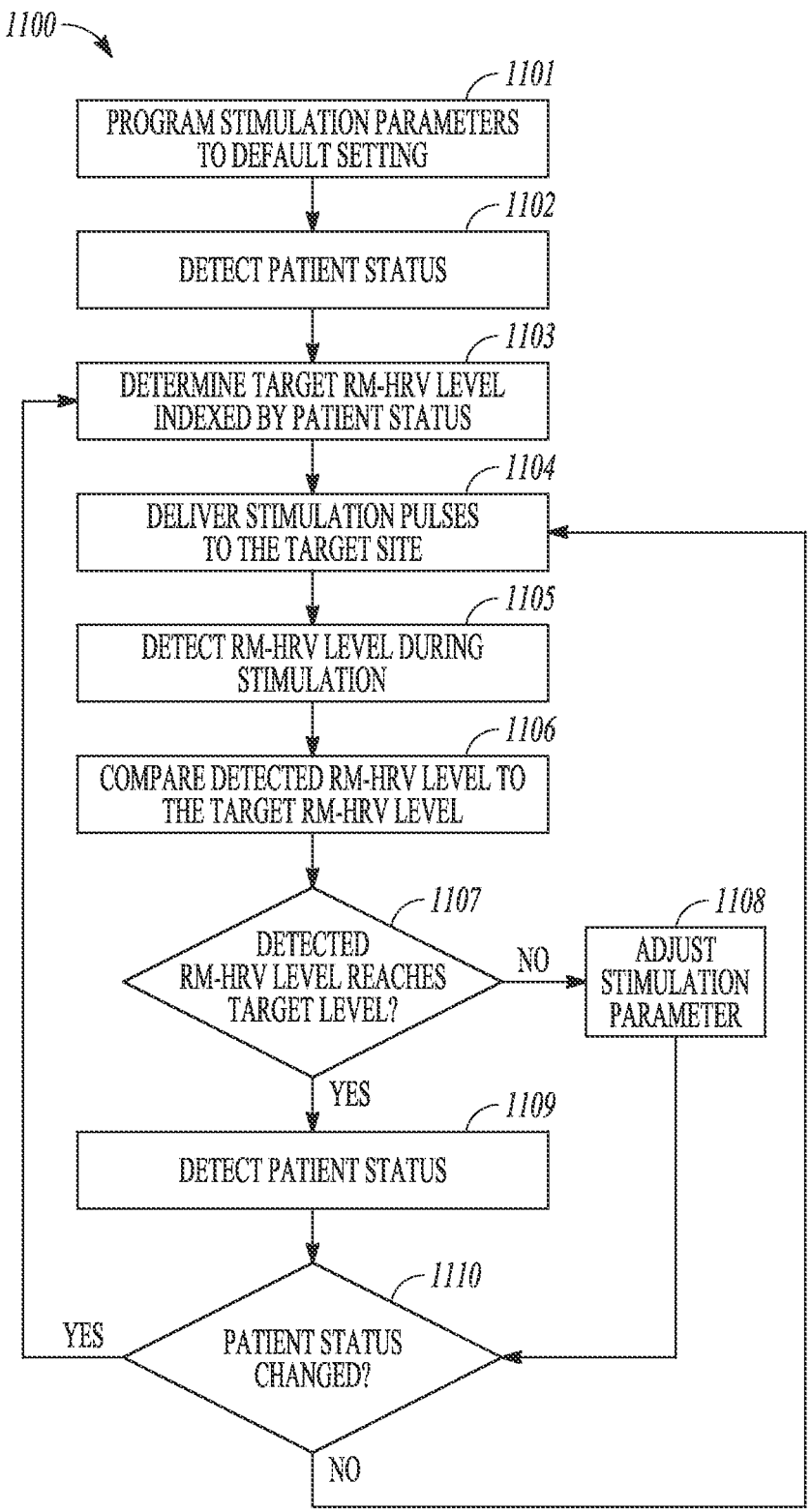
FIG. 11 illustrates, by way of example, a method for stimulating a target site to treat hypertension using patient status-indexed RM-HRV.

FIG. 11 illustrates, by way of example, a method 1100 for stimulating a target site to treat hypertension using patient status-indexed RM-HRV. The method 1100 represents an embodiment of the method 700 for AHT stimulation therapy. The method begins with programming one or more stimulation parameters to default setting at 1101. The parameters may be programmed empirically using information such as patient's health status and disease records, the patient's AHT stimulation treatment history, or population-based effectiveness of the AHT therapy. A patient status can be subsequently detected at 1102. The patient status can include physiologic status or non-physiologic status. Examples of physiologic status include a respiration rate, an activity levels, a sleeping state, a posture, and a disease state such as pulmonary edema, congested heart failure, and sleep apnea. Examples of non-physiologic status may include circumstantial and contextual information such as patient location, ambient temperature, humidity, atmospheric pressure, air pollution index, patient's normal sleep time, and patient's medical history. The patient status can be detected using sensors. In an embodiment, an accelerometer can be used to detect the patient posture and the activity level.

At 1103, a target RM-HRV indexed by patient status can be determined using the detected patient status. The target RM-HRV, represented as a RM-HRV threshold or a desirable RM-HRV range, indicates the desired amount of reduction in blood pressure, and therefore the effectiveness of the AHT therapy. Generally, the patient status may affect the respiration-mediated heart rate variation. For example, a higher activity state may be accompanied by an increased sympathetic tone and decreased parasympathetic tone, thereby causing a reduced RM-HRV level compared to lower-activity state or during sleep. In another example, the RM-HRV level during sleep, particularly non-rapid-eye-movement (non-REM) sleep, is generally higher than during awakening due to the suppressed sympathetic activity and increased parasympathetic activity during sleep.

The target RM-HRV level is indexed by the patient status, such that at different patient status, the target RM-HRV may be different. For example, in an embodiment, a lower target RM-HRV is chosen if the patient's respiration rate in higher, or if the patient's activity level is higher. In contrast, a higher target RM-HRV is chosen if the patient is in a non-REM sleep state. In determining the target RM-HRV level, a patient status—target HRV map may be created and stored such as in the memory circuit 205. The patient status—target HRV map comprises a plurality of patient status including, for example, multiple levels of activity or ranges of respiration rate, each patient status being mapped to a target RM-HRV level. In some embodiments, the patient status-target RM-HRV map may be implemented as a look-up table, a hash table, an association map, or other data structure with searchable entries stored such as in the memory circuit 205. Then, for the detected patient status 1102, a target RM-HRV may be determined by associating the detected present patient status to the corresponding RM-HRV using the patient status-target RM-HRV map. In some embodiments, the respiration-mediated heart rate levels stored in the patient status-HRV map are HRV threshold values ($HRV_T$) indexed by the set of patient status. In some other embodiments, the respiration-mediated heart rate levels stored in the patient status-HRV map are ranges of desirable HRV values indexed by the set of patient status.

At 1104, stimulation pulses are delivered to the target site according to the programmed stimulation parameters. During the stimulation, respiration and heart rates are sensed and RM-HRV level is detected at 1105. In an embodiment, the RM-HRV may be determined using the method 800. In some embodiments, in determining the RM-HRV level, the respiration signal and the heart rates are synchronized, and only the detected heart rates or intervals during the respiration cycles of specified duration are used in computing the RM-HRV.

At 1106, the detected RM-HRV is compared to the target RM-HRV indexed by the present patient status. In an embodiment, the difference between the detected HRV and the target RM-HRV is computed. At 1107, the comparison, such as the difference, between the detected RM-HRV and the target RM-HRV is checked against a criterion. If the detected RM-HRV is less than the target, patient status-indexed RM-HRV by a specified tolerance level, the stimulation strength is deemed insufficient to cause desirable blood pressure reduction. Then at 1108, the one or more stimulation parameters can be adjusted to increase the stimulation strength. If, however, the detected RM-HRV is greater than the target, patient status-indexed RM-HRV by a specified tolerance level, the stimulation strength is deemed sufficient to cause desirable blood pressure reduction, and the present parameters may remain unchanged. After the parameter adjustment at 1108, or keeping parameter unchanged at 1107, the patient status is rechecked at 1109. The redetected patient status is compared to the previously detected patient status at 1110. If the patient status does not change, then the stimulation may be delivered according to the most recent stimulation parameters at 1104. However, if the patient status has changed from the previous status, then a new target RM-HRV level indexed by the present patient status may be determined at 1103, and the stimulation can then resumed from therein.

The above detailed description is intended to be illustrative, and not restrictive. Other embodiments will be apparent to those of ordinary skills in the art upon reading and understanding the above description. The scope of the invention should, therefore, be determined with references to the appended claims, along with the full scope of equivalents to which such claims are entitled.

What is claimed is:

1. A system, comprising:
a stimulator configured to generate stimulation pulses;
a respiration signal detector configured to sense a respiration signal;
a heart rate variation detector configured to sense a physiologic signal indicative of a heart rate, detect a plurality of heart rates during the delivery of the stimulation pulses to a target site, synchronize the detected heart rates with one or more respiration cycles from the sensed respiration signal by compensating system lag and physiologic lag between the detected heart rates and the respiration signal, and determine a respiration-mediated heart rate variation using the synchronized heart rates;
a memory circuit configured to store one or more stimulation parameters;
a controller circuit coupled to the stimulator and the heart rate variation detector, the controller circuit configured to control the delivery of the stimulation pulses using the respiration-mediated heart rate variation.

2. The system of claim 1, wherein the heart rate variation detector is configured to sense at least one of an electrocardiogram, an intracardiac electrogram, and a cardiac mechanical activation signal.

3. The system of claim 1, wherein the respiration signal detector is configured to receive an intrathoracic impedance signal, and detect at least one of the one or more respiration cycles from the intrathoracic impedance signal, and an inspiration phase and an expiration phase from the one or more respiration cycles.

4. The system of claim 3, wherein the heart rate variation detector is configured to calculate a variation between the heart rates during the inspiration phase and the heart rates during the expiration phase.

5. The system of claim 4, wherein the heart rate variation detector is configured to calculate a heart rate range within the one or more respiration cycles, the heart rate range including a difference between a representative heart rate during the inspiration phase and a representative heart rate during the expiration phase.

6. The system of claim 4, wherein the heart rate variation detector is configured to calculate at least one of a variance or a spreadness measure of the heart rates within the one or more respiration cycles.

7. The system of claim 1, wherein the controller circuit is configured to adjust a stimulation strength by adjusting the one or more stimulation parameters including a pulse width, a pulse frequency, a pulse amplitude, a pulse duty cycle, a therapy-on period, or a therapy-off period.

8. The system of claim 7, wherein the controller circuit is configured to maintain or decrease the stimulation strength in response to the respiration-mediated heart rate variation exceeding a first threshold, or increase the stimulation strength in response to the respiration-mediated heart rate variation falling below a second threshold.

9. The system of claim 1, further comprising a target heart rate variation determination circuit coupled to the memory circuit, the target heart rate variation determination circuit configured to determine a patient-status indexed respiration-mediated heart rate variation using the present patient status; and wherein
the memory circuit is further configured to store a plurality of respiration-mediated heart rate variation levels, a set of patient status, and an association map associating each of the patient status to one of the respiration-mediated heart rate variation levels; and
the controller circuit is configured to adjust the one or more stimulation parameters using a comparison of the detected respiration-mediated heart rate variation and the target heart rate variation.

10. A method of treating hypertension, comprising:
sensing a physiologic signal indicative of a heart rate;
detecting a plurality of heart rates from the physiologic signal;
sensing a respiration signal and detecting one or more respiration cycles from the respiration signal;
synchronizing the detected heart rates with one or more respiration cycles from the sensed respiration signal by compensating system lag and physiologic lag between the detected heart rates and the respiration signal;
determining a respiration-mediated heart rate variation using the synchronized heart rates;
programming one or more stimulation parameters using the respiration-mediated heart rate variation;
generating stimulation pulses in accordance with the one or more stimulation parameters; and
delivering the stimulation pulses to the target site.

11. The method of claim 10, wherein delivering the stimulation pulses to the target site includes delivering the stimulation pulses to at least one of a baroreceptor region and a vagus nerve region.

12. The method of claim 10, wherein delivering the stimulation pulses to the target site includes delivering the stimulation pulses subcutaneously or transvenously.

13. The method of claim 10, wherein sensing the physiologic signal indicative of the heart rate includes sensing at least one of an electrocardiogram, an intracardiac electrogram, and a cardiac mechanical activation signal.

14. The method of claim 10, wherein sensing the respiration signal includes sensing an intrathoracic impedance signal and detecting at least one of one or more respiration cycles from the intrathoracic impedance signal and an inspiration phase and an expiration phase from the one or more respiration cycles.

15. The method of 14, wherein determining the respiration-mediated heart rate variation includes:
determining a plurality of heart rates during the inspiration phase and a plurality of heart rates during the expiration phase; and
calculating the heart rate variation between the heart rates during the inspiration phase and the heart rates during the expiration phase.

16. The method of claim 15, wherein calculating the variation includes determining a heart rate range within the one or more respiration cycles, the heart rate range including a difference between a representative heart rate during the inspiration phase and a representative heart rate during the expiration phase.

17. The method of claim 15, wherein calculating the heart rate variation includes determining at least one of a variance or a spreadness measure of the heart rates within the one or more respiration cycles.

18. The method of claim 10, wherein programming the one or more stimulation parameters includes maintaining or decreasing values of the one or more stimulation parameters to reduce stimulation strength in response to the respiration-mediated heart rate variation exceeding a first threshold, or increasing the values of the one or more stimulation parameters to increase the stimulation strength in response to the respiration-mediated heart rate variation falling below a second threshold, the one or more stimulation parameters including a pulse width, a pulse frequency, a pulse amplitude, a pulse duty cycle, a therapy-on period, or a therapy-off period.

19. The method of claim 10, further comprising:
creating an association map between a plurality of respiration-mediated heart rate variation levels and a set of patient status, the association map associating each of the patient status to one of the respiration-mediated heart rate variation levels, the patient status including one or more of a respiration rate, an activity levels, a sleeping state, a posture, and a disease state;
detecting a present patient status;
determining a target heart rate variation using the present patient status and the association map;
wherein programming the one or more stimulation parameters includes adjusting the one or more stimulation parameters using a comparison of the detected respiration-mediated heart rate variation and the target heart rate variation.

* * * * *